United States Patent
Highsmith et al.

(10) Patent No.: US 6,870,061 B2
(45) Date of Patent: *Mar. 22, 2005

(54) CONTINUOUS PROCESS AND SYSTEM FOR PRODUCTION OF GLYCIDYL NITRATE FROM GLYCERIN, NITRIC ACID AND CAUSTIC AND CONVERSION OF GLYCIDYL NITRATE TO POLY(GLYCIDYL NITRATE)

(75) Inventors: Thomas K. Highsmith, North Ogden, UT (US); Harold E. Johnston, Brigham City, UT (US)

(73) Assignee: Alliant Techsystems Inc., Edina, MN (US)

( * ) Notice: Subject to any disclaimer, the term of this patent is extended or adjusted under 35 U.S.C. 154(b) by 139 days.

This patent is subject to a terminal disclaimer.

(21) Appl. No.: 10/340,167

(22) Filed: Jan. 10, 2003

(65) Prior Publication Data

US 2004/0138481 A1 Jul. 15, 2004

(51) Int. Cl.$^7$ .................... C07D 303/22; C07D 303/36; G08G 65/10

(52) U.S. Cl. ................ 549/551; 549/555; 549/560; 525/406; 525/410; 528/403; 528/408; 528/420

(58) Field of Search ................................ 549/551, 555, 549/560; 525/406, 410; 528/403, 408, 420

(56) References Cited

U.S. PATENT DOCUMENTS

| 5,120,827 A | 6/1992 | Willer et al. |
| 5,136,062 A | 8/1992 | Millar et al. |
| 5,145,974 A | 9/1992 | Paul et al. |
| 6,362,311 B1 | 3/2002 | Highsmith et al. |

FOREIGN PATENT DOCUMENTS

WO    WO 01/29111 A1    4/2001

OTHER PUBLICATIONS

UK Patent Office Search Report dated Jun. 18, 2004.
French Patent Office Search Report dated Aug. 26, 2004.
Naoum, Phokion, Nitroglycerine and Nitroglycerine Explosives. The World Wide Chemical Translation Series. 1928, pp. 161–179, Number One. The Williams & Wilkins Company, Baltimore.
Urbanski, Tadeusz, Chemistry and Technology of Explosives. date unknown, pp. 90–140, vol. 2. Pergamon Press, Oxford, 1965.

*Primary Examiner*—Ba K. Trinh
(74) *Attorney, Agent, or Firm*—TraskBritt

(57) ABSTRACT

A continuous and scalable process for producing glycidyl nitrate, or glyn, from glycerin, nitric acid, and caustic wherein the process includes the reaction of glycerin and nitric acid to form dinitroglycerin and the reaction of dinitroglycerin with caustic, such as sodium hydroxide, system for producing the inventive material is also disclosed. The vessel, a second reaction vessel, and a separation apparatus.

83 Claims, 5 Drawing Sheets

CONTINUOUS PROCESS AND SYSTEM FOR PRODUCTION OF GLYCIDYL NITRATE FROM GLYCERIN, NITRIC ACID AND CAUSTIC AND CONVERSION OF GLYCIDYL NITRATE TO POLY(GLYCIDYL NITRATE)

GOVERNMENT LICENSE RIGHTS

The U.S. Government has a paid-up license in this invention and the right in limited circumstances to require the patent owner to license others on reasonable terms as provide for by the terms of Contract F04611-99-C-0010.

BACKGROUND OF THE INVENTION

1. Field of the Invention

The present invention relates to a process for the production of glycidyl nitrate. More particularly, the present invention relates to a scalable, continuous process for the production of glycidyl nitrate from glycerin, nitric acid and caustic.

2. State of the Art

It has been recognized that poly(glycidyl nitrate) is an excellent energetic polymer that may be used as an explosive agent, a propellant, or the like. However, conventional production of poly(glycidyl nitrate), or "PGN" for short, is complicated, may be dangerous, and is oftentimes expensive. The costs and danger involved in the production of PGN limit the use of PGN as a viable explosive agent or propellant.

A process for producing improved PGN to be used as a binder in high-energy compositions such as propellants, explosives, gasifiers, and the like is disclosed in U.S. Pat. No. 5,120,827, issued to Willer et al. Willer et al. disclose that PGN may be formed by a combination of a reaction mixture, comprising a polyol initiator and an acid catalyst, with glycidyl nitrate ("glyn"):

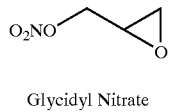

Glycidyl Nitrate

Addition of a glycidyl nitrate monomer to the reaction mixture at a rate essentially equivalent to on allows the formation of PGN to occur. A solvent, such as methylene chloride, ed to the reaction mixture with the glycidyl nitrate.

Unfortunately, production of PGN by the Willer et al. method is limited by the availability of glycidyl nitrate, which must be produced or procured to make PGN. Glycidyl nitrate is an expensive monomer and is not available commercially. In addition, purification methods used to prepare glycidyl nitrate are dangerous because they require distilling an unstable explosive. Furthermore, these purification methods are unable to produce glycidyl nitrate having a purity that may be used in the Willer et al. PGN production process.

For example, glycidyl nitrate may be produced in a multistep process by the nitration of epichlorohydrin with nitric acid, followed by the recyclization of the nitrated epichlorohydrin with a base to form glycidyl nitrate. During the cyclization step, however, an appreciable amount of epichlorohydrin is regenerated along with the glycidyl nitrate. The presence of epichlorohydrin with the glycidyl nitrate during polymerization to PGN reduces the energetic characteristics of the PGN and also undesirably chances the physical properties of the PGN. The presence of impurities of any kind is undesirable in the subsequent polymerization. Therefore, the epichlorohydrin must be distilled or otherwise removed from the glycidyl nitrate prior to polymerization. Additionally, glyn contains a thermally unstable oxirane ring that further sensitizes it toward deleterious thermal processes. This, in conjunction with the inherent instability of nitrate esters, makes the distillation process unsafe and expensive for large-scale production processes. Other methods of purification, such as chromatography or crystallization, also are not acceptable. Thus, the production of glycidyl nitrate from the nitratation of epichlorohydrin is a dangerous, inefficient, and expensive process for the production of glycidyl nitrate in large quantities using commercial-scale processing operations.

In another known process, distilled glycidol is treated with nitrogen pentoxide ($N_2O_5$) at a temperature of between $-10°$ C. and $-70°$ C. in an inert organic solvent such as dichloromethane (methylene chloride) to form glycidyl nitrate and nitric acid. To recover the glycidyl nitrate, the nitric acid is separated from the mixture. Millar et al. describe this process in U.S. Pat. No. 5,136,062. The production of glycidyl nitrate by the Millar et al. process is typically carried out in batch reactions at low temperatures. Millar et al. also describe a continuous mode of producing glycidyl nitrate, which is disclosed in U.S. Pat. No. 5,145,974. However, these processes do not lend themselves to the large-scale production of glycidyl nitrate because of the expenses involved and difficulty of employing the reagents in a commercial-scale production process. For instance, the glycidol used in this process must be procured as a specialty synthesis material and, as such, is expensive. In addition, glycidol can polymerize catastrophically above ambient temperature and, therefore, must be stored at reduced temperatures. Similarly, the use of nitrogen pentoxide is expensive because it must be prepared using specialized equipment and must be stored at cryogenic temperatures. Low temperature synthesis processes are costly due to the operating and equipment costs incurred to ensure that low temperatures are maintained for the synthesis reactions.

The processes currently available for producing glycidyl nitrate are not economically feasible for the large-scale commercial production of glycidyl nitrate are not economically feasible for the large-scale commercial production of glycidyl nitrate. Furthermore, the known methods of producing glycidyl nitrate are inherently dangerous. Therefore, a safe and relatively inexpensive process for producing glycidyl nitrate in large quantities is desirable. It would also be desirable to develop a commercial process for producing glycidyl nitrate having purity sufficient for use in a PGN process without the need for further distillation or reaction.

SUMMARY OF THE INVENTION

The present invention relates to the production of glycidyl nitrate from glycerin, nitric acid, and caustic using a scalable, continuous production process. The purity of the glycidyl nitrate produced using the process of the present invention is sufficient for use with a commercial PGN production process.

Glycidyl nitrate may be produced from a series of reactions involving glycerin, nitric acid, and caustic. In one embodiment of the present invention, glycerin and nitric acid are reacted in a first reaction vessel to produce nitrates esters and, predominantly, 1,3-dinitroglycerin. Unreacted nitric is neutralized in a second reaction vessel by the addition of a caustic, such as sodium hydroxide or lye, to produce sodium nitrate and water. The 1,3-dinitroglycerin is partly immiscible in the neutralized brine and is decanted into a third vessel in which the 1,3-dinitroglycerin is further reacted with additional caustic to form glycidyl nitrate. The glycidyl nitrate is separated from the sodium nitrate and water using a separation apparatus, such as a decanter or other equipment.

In another embodiment, the process of the present invention may be carried out using two continuously overflowing stirred reaction vessels and one decanter. In this embodiment, the glycerin is nitrated to 1,3-dinitroglycerin in the first reaction vessel. The overflow is reacted with excess base in the second reaction vessel to neutralize the excess nitric acid and form glycidyl nitrate from the 1,3-dinitroglycerin. The overflow from the second reaction vessel flows into the decanter, which separates the immiscible organic phase from the basic aqueous solution.

Each of the reactions occurring during the process of the present invention may be conducted from about 0° C. to about 25° C. The preferred temperature for the nitration reaction is about 5° C. and the preferred temperature for causticization and separation is about 25° C. The ability to perform the process of the present invention at ambient or near-ambient temperatures offers significant advantages over conventional glycidyl nitrate processes that are typically carried out at low temperatures, for instance, between −10° C. and −70° C.

The continuous nature of the process of the present invention is also advantageous. Compared to batch reactions, the continuous process reduces labor costs for a production facility and allows the continuous production of product as needed. In addition, the continuous process may be scaled up or down using conventional chemical processing equipment to meet the needs of a PGN production facility or the market. Furthermore, the process may be run in existing facilities, such as conventional Biazzi nitrators, which makes the process viable from an industrial perspective.

An organic solvent may be added to the reactions in the inventive process to promote safety. The energetic nature of the mixed nitrate esters produced using the process of the present invention may lead to explosive reactions within the process. The addition of an organic solvent, such as dichloromethane (methylene chloride) or dichloroethane, to the reaction process dilutes and moderates the reactions and provides a significant measure of safety to the process since the organic solvent absorbs the heat of the reaction and boils before dangerous temperatures are reached. In addition, the boiling, gaseous organic solvent removes the decomposition catalyst, nitrogen oxide ("$NO_x$"), making the reaction stable and suitable for use in commercial environments.

Safety is also promoted by use of the present invention because the volume of reagents undergoing reaction and, thus, the size of the reactions may be kept small. The continuous nature of the process allows the production of glycidyl nitrate to proceed continuously; thus, large batch reactions of conventional processes need not be undertaken to create a desired amount of glycidyl nitrate that the smaller reaction continuous process of the present invention may produce in the same amount of time. In addition, the glycidyl nitrate produced using the process of the present invention is sufficiently pure to use with PGN production processes. The purity eliminates the need to further react or distill the glycidyl nitrate, thereby avoiding dangerous and costly purification processes employed with other lycidyl nitrate processes to produce a product of sufficient purity for PGN production.

The production of glycidyl nitrate using the process of the present invention also provides enhanced efficiency over other glycidyl nitrate production processes. It has been found that the continuous process of the present invention achieves an unexpectedly high nitration yield of at least about 50 percent, and as high as about 90 percent, as compared to the 50 to 60 percent nitration yield typically found in batch production processes. It is believed that skewed kinetics of the continuous process account for the increased nitration yield realized using the production process of the present invention.

The production of glycidyl nitrate using the process of the present invention is also an environmentally clean process. The waste products are sewerable and may be treated using known wastewater treatment facilities. In addition, the solvent used in the process does not create an unwanted waste byproduct because the solvent and the glycidyl nitrate may be separated from other reaction products and passed to a PGN process for a polymerization reaction. Solvent is necessary in the polymerization reaction to get the desired kinetics and viscosity. The solvent extracted from the PGN process may then be recycled back for use in the glycidyl nitrate process of the present invention.

The process of the present invention reduces the costs associated with the production of glycidyl nitrate in a number of ways. The reagents used in the process are relatively inexpensive and readily, commercially available. The continuous nature of the process reduces labor costs and the conventional equipment used in the process eliminates the need for expensive, customized processing equipment. Most notably, the present invention may be easily carried out in a commercial nitrator, such as that produced by Biazzi SA (Montreux, Switzerland). The lack of output of hazardous waste streams by the inventive process eliminates the need and expense of waste processing equipment or costly disposal techniques. Furthermore, since the reactions used in the present process may occur at temperatures between about 0° C. and about 25° C., the costs of low-temperature reaction equipment required by other glycidyl nitrate production processes are eliminated.

Thus, a number of factors make the process of the present invention a more viable alternative for the production of glycidyl nitrate than conventional processes, including, but not limited to: the continuous nature of the process; the inherent safety associated with the process; the reduced production costs of the process; the increased nitration yields associated with the process; the thermal savings realized with the process; and the improved purity of the glycidyl nitrate produced by the process, which allows the glycidyl nitrate to be used in a PGN production process without further purification.

DESCRIPTION OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

The present invention relates to the production of glycidyl nitrate, or "glyn", from glycerin, nitric acid, and caustic using a continuous production process. Using the process of the present invention, glycidyl nitrate may be produced continuously using conventional chemical processing equipment. For example, the process may be run in conventional nitrate ester process plants without having to build new facilities. The reagents used to make glycidyl nitrate according to the present invention are readily available on the open market and are relatively inexpensive. In addition, the continuous nature of the process reduces the labor costs associated with the production of glycidyl nitrate. Therefore, the continuous process of the present invention is less expensive than other processes used to produce glycidyl nitrate. The process of the present invention also provides a safe process for producing glycidyl nitrate while reducing the risks of adverse reaction by the products and other intermediate chemicals produced within the process. Furthermore, the process of the present invention is more efficient at the production of glycidyl nitrate than other processes and the wastes produced by the process are sewerable, eliminating the need for waste treatment processes.

It has been found that glycidyl nitrate may be produced from glycerin, nitric acid, and a caustic such as, for example, sodium hydroxide (NaOH) in a single pass reaction system. The production of glycidyl nitrate from these chemicals proceeds as follows:

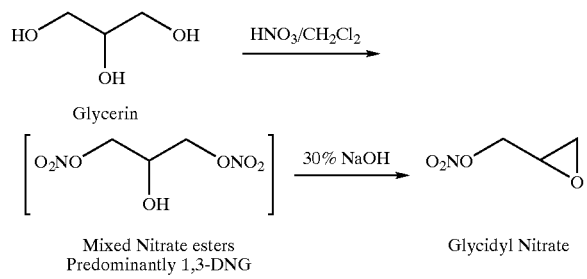

As depicted above, glycerin is reacted with nitric acid ($HNO_3$) to form mixed nitrate esters and, predominantly, 1,3-dinitroglycerin (1,3-DNG). The continuous mode of the present invention almost completely produces a desired isomer of 1,3-DNG rather than the statistical distribution of isomers that is achieved when the reaction is performed in batch mode. Reaction of the 1,3-DNG with sodium hydroxide (NaOH) produces glycidyl nitrate. 100281 Production of glycidyl nitrate based on this reaction chemistry may be performed in a continuous reaction or process system. Feeding the chemicals to a single-pass reaction system, the desired product—glycidyl nitrate—maybe produced as a product stream from the system. The glycidyl nitrate produced by the process may be readily polymerized into PGN without the need for distillation or additional reactions for further purification.

Figure 1:
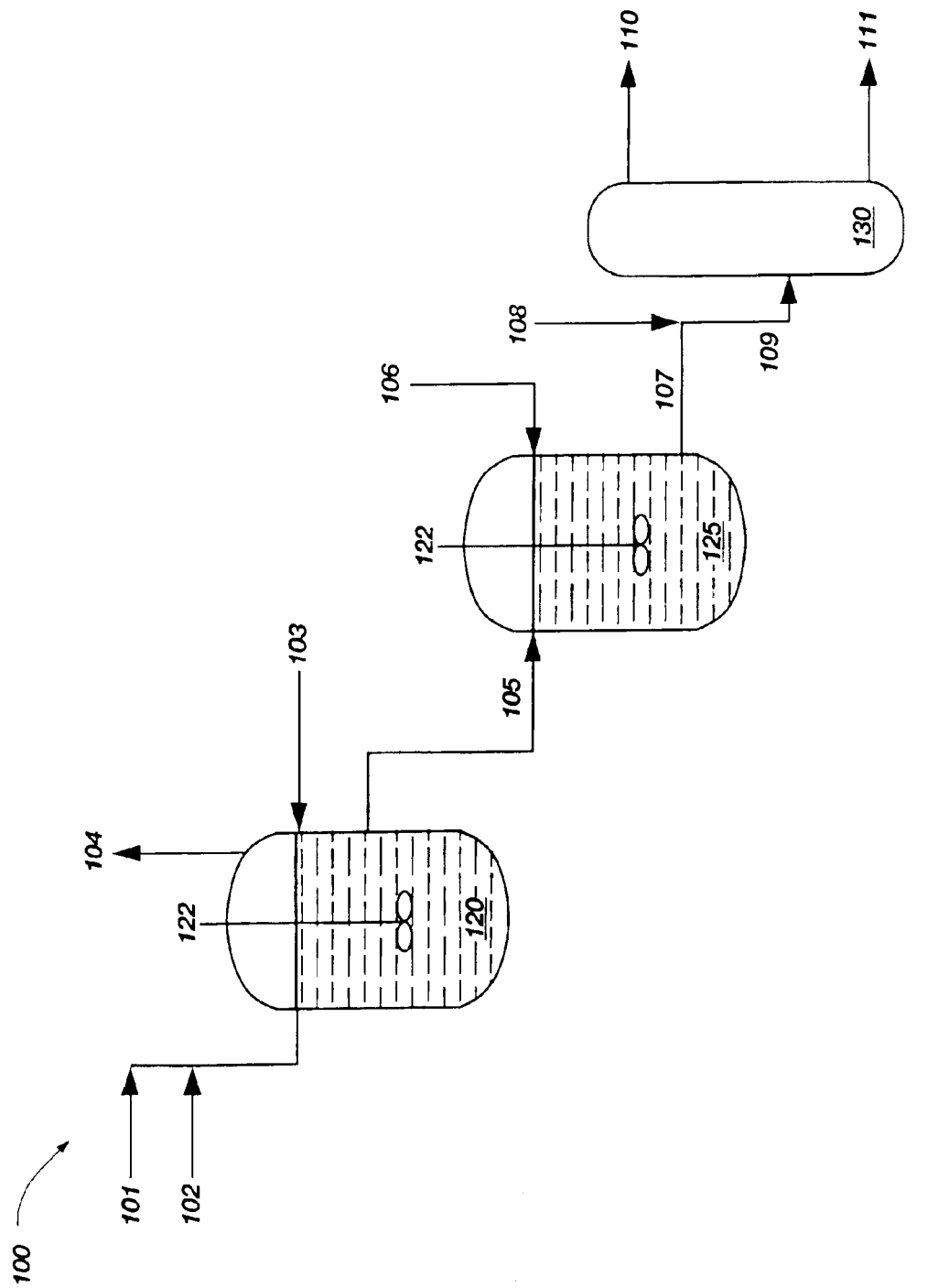
FIG. 1 illustrates a process flow diagram of a glycidyl nitrate production process according to an embodiment of the present invention.

A flow diagram illustrating an exemplary process system for carrying out the present invention is illustrated in FIG. 1.

In the process, the reagents (the glycerin, the nitric acid, and the caustic) are mixed in reaction vessels and the resulting products are separated. More specifically, the process system 100 includes a first reaction vessel 120, a second reaction vessel 125, and a separation apparatus 130. A stirring mechanism 122 may optionally be used with the first reaction vessel 120 and second reaction vessel 125 to aid in the mixing of any reagents or products in the respective reaction vessel. The reaction vessels may include any type of reaction vessel for use in a continuous chemical production process, such as a continuous overflowing reaction vessel. The reaction vessels may be designed to provide a desired residence time and to remove heat generated during the causticization reaction. For sake of example only, a nitrator may be used as the reaction vessel. The separation apparatus 130 may include any type of separation apparatus that is used to separate organic material from nonorganic material, such as a dynamic or static separation apparatus. For sake of example only, the separation apparatus 130 may be a column, a decanter, a centrifuge, weir tanks, a static separator, or a bucket. The exact makeup of the reaction vessels 120 and 125 and separation apparatus 130 is not critical to the operability of the present invention.

The first reaction vessel 120 is preferably a nitrator, such as a conventional Biazzi nitrator, known in the art. Glycerin 101, nitric acid 102, and air 103 may be fed to the first reaction vessel 120 and mixed to promote a reaction. The reaction may be performed at a temperature ranging from approximately 0° C. to approximately 25° C. and preferably is performed at approximately 5° C. The stirring mechanism 122 may be used to mix the reagents fed to the first reaction vessel 120 for promoting the reaction therein. Glycerin 101 and nitric acid 102 fed to the first reaction vessel 120 may react to form 1,3-dinitroglycerin and water. To improve safety, the nitric acid 102 may be fed to the first reaction vessel 120 with a solvent, such as dichloromethane or dichloroethane. Air 103 may be used to purge $NO_X$, which otherwise may cause the reaction to explode, from the first reaction vessel through a vent 104. When combined with the nitric acid 102 and glycerin 101, the solvent dilutes the energetic monomer nitric ester glyn, thereby improving the safety of the reaction process. However, this solvent is not critical to the operability of the process of the present invention. A product stream 105 leaving the first reaction vessel 120 may include 1,3-dinitroglycerin and water formed by the reaction within the first reaction vessel 120, as well as unreacted nitric acid. The product stream 105 exiting the first reaction vessel 120 may also include dichloromethane if a solvent is used to improve the safety of the system.

The product stream 105 is fed to a second reaction vessel 125 with a sodium hydroxide solution (NaOH) 106. The sodium hydroxide solution 106 may be a solution having approximately 25–30% NaOH. The product stream 105 and sodium hydroxide solution 106 may be mixed within the second reaction vessel 125 by the stirring mechanism 122 to help promote reaction of the components in the second reaction vessel 125. The reaction may be performed at a temperature ranging from approximately 0° C. and preferably is performed at approximately 24° C. The sodium hydroxide solution 106 reacts with the product stream 105 to produce glycidyl nitrate. Nitric acid and dinitroglycerin in the product stream 105 are neutralized by the sodium hydroxide solution 106 and converted to glycidyl nitrate.

A second product stream 107 leaving the second reaction vessel 125 is optionally combined with a second solvent stream 108 of dichloromethane to form product stream 109, which is fed to the separation apparatus 130 for separating glycidyl nitrate from the second product stream 107. The separation apparatus 130, such as a decanter, separates glycidyl nitrate and dichloromethane from other components of the second product stream 107, resulting in a final product stream 111 of glycidyl nitrate mixed with dichloromethane and a brine 110 waste stream.

Figure 3:
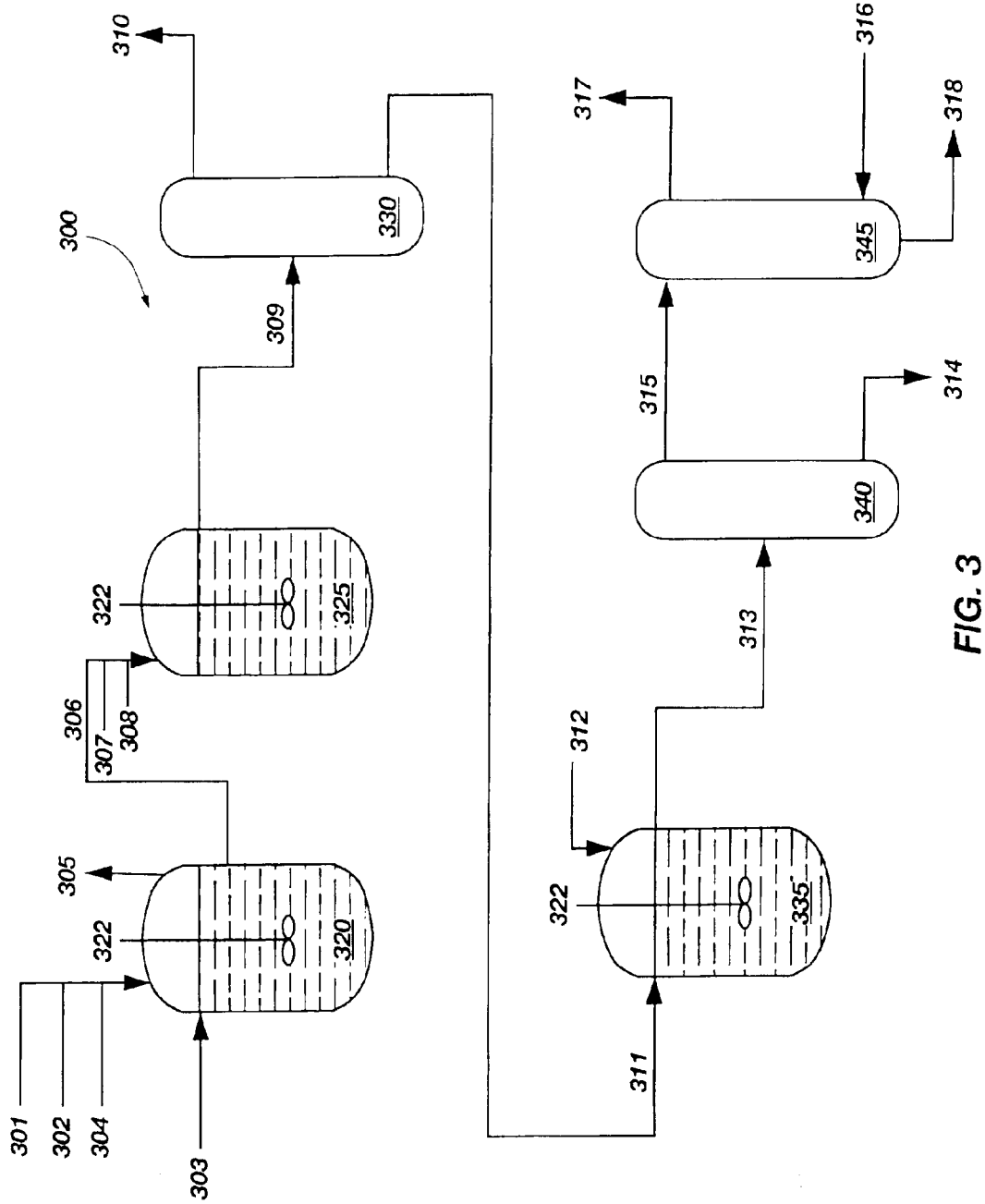
FIG. 3 illustrates a process flow diagram of a glycidyl nitrate production process according to another embodiment of the present invention.

A flow diagram illustrating another embodiment of the processing equipment and component streams that may be used to carry out the process of the present invention is illustrated in FIG. 3. The illustrated system 300 includes three reaction vessels, three separation columns, and various reagent and the product streams. It is understood that other process equipment configurations may be used in place of systems 100 or 300 for carrying out the various embodiments of the present invention.

The reaction vessels of system 300 include a first reaction vessel 320, a second reaction vessel 325, and a third reaction vessel 335. Standard reaction vessels, such as continuous overflowing reaction vessels, may be used with the present invention. Each of the reaction vessels may include a stirring mechanism 322 as used with chemical production processes for stirring or mixing reagents within a respective reaction vessel.

The separation columns illustrated for use with system 300 include a first separation column 330, a second separation column 340, and a third separation column 345. The separation columns used to carry out the various embodiments of the present invention may include any type of stripping or separation column used to separate chemical components.

Glycerin, nitric acid, and a caustic are combined within system 300 to produce glycidyl nitrate. Glycerin 301 and nitric acid 304 may be combined within the first reaction vessel 320. The reaction may be performed at a temperature ranging from approximately 0° C. to approximately 25° C. and preferably is performed at approximately 5° C. To improve safety, a solvent 302, such as dichloromethane or dichloroethane, may be added to the first reaction vessel 320 with the glycerin 301 and nitric acid 304. Use of the solvent 302 dilutes the energetic monomer nitrate ester glyn produced by the combination of glycerin 301 with nitric acid 304, thereby improving the safety of system 300. While the solvent 302 may improve the safety, the solvent 302 is not critical to the operability of the present invention. Air 303 may also be fed to the first reaction vessel 320 to aid in the reaction process and remove unwanted gases. A vent 305 in the first reaction vessel may allow fumes and built-up gases resulting from any reaction therein to escape the first reaction vessel 320. For instance, the vent 305 may allow the escape of air, dichloromethane, and nitric acid. A stirring mechanism 322 may optionally be used to ensure that the reagents added to the first reaction vessel 320 are thoroughly mixed.

A product stream 306 from the first reaction vessel 320 is fed to a second reaction vessel 325. Product stream 306 comprises products from reactions occurring within the first reaction vessel 320, including dinitroglycerin, nitric acid, and water. If a solvent 302 was added to the first reaction vessel 320, some solvent 302 may also pass to the second reaction vessel 325 in product stream 306. In addition to product stream 306, caustic 308 is added to the second reaction vessel 325. The product stream 306 and caustic 308 are both fed to the second reaction vessel 325 at a temperature of about 5° C. and are mixed at a temperature of about 5° C. The caustic 308 used with the process of the present invention is preferably sodium hydroxide (NaOH). Additional solvent 307 may also be added to the second reaction vessel 325 to improve safety and reduce the chances of a catastrophic event from occurring due to the energetic reactions associated with the nitration process. However, the solvent 307 is not critical to the operability of the present invention. A stirring mechanism 322 may optionally be used to ensure that the reagents added to the second reaction vessel 325 are thoroughly mixed.

A product stream 309 from the second reaction vessel 325 is directed to a first separation column 330. Product stream 309 may include dichloromethane, nitric acid, dinitroglycerin, water, and sodium nitrate. Portions of the water and sodium nitrate in product stream 309 are separated within the first separation column 330 and discharged as a brine 310 or waste stream. A product stream 311 from the first separation column 330 is fed to a third reaction vessel 335.

Product stream 311 is reacted with caustic 312, such as sodium hydroxide, within the third reaction vessel 335. The product stream 311 and caustic 312 are fed to the third reaction vessel 335 at a temperature of about 5° C. Product stream 311 may include nitric acid, dinitroglycerin, and sodium nitrate. The reaction with the caustic 312 may be performed at a temperature ranging from approximately 0° to approximately 25° C., and preferably is performed at approximately 24° C. If a solvent 302 was used previously in the process, product stream 311 will also include solvent 302. The reaction between product stream 311 and caustic 312 within the third reaction vessel 335 produces a product stream 313 including water, sodium hydroxide, glycidyl nitrate, sodium nitrate, sodium chloride, and solvent 302 if solvent 302 was previously used in the process.

Product stream 313 is fed to a second separation column 340 to remove water, sodium hydroxide, and sodium nitrate from product stream 313. Brine 314 is removed as bottoms from the second separation column 340. A product stream 315 from the second separation column 340 is fed to a third separation column 345 to retrieve the desired product—glycidyl nitrate.

Product stream 315 typically includes glycidyl nitrate and sodium nitrate. If a solvent 302 is used in the process, product stream 315 will also include solvent 302. In addition to feeding the product stream 315 to the third separation column 345, sodium chloride 316 (NaCl) is added to the third separation column 345 in solution form. The addition of sodium chloride 316 in solution removes the sodium nitrate from product stream 315. The resulting streams exiting the third separation column 345 include brine 317 and a final product stream 318. The brine 317 includes sodium chloride 316 in solution and sodium nitrate stripped from product stream 315. The final product stream 318 includes the desired end product—glycidyl nitrate—and solvent 302 if a solvent 302 was used in the process.

The reactions in the process of the present invention may be performed at temperatures between 0° C. and 25° C. For example, the temperature of the reaction performed in the nitrator may be low, such as about 5° C., while the temperature at which the causticization reaction is performed is about 25° C. (about 75° F.). Unlike other glycidyl nitrate production processes, extremely low temperatures are not necessary for the present process. Thus, the costs associated with maintaining extremely low temperatures are eliminated, making the present process more economically feasible than other processes.

Glycidyl nitrate may be produced from the interaction of chemical reagents glycerin, nitric acid, and caustic using the continuous production processes illustrated in FIGS. 1 and 3, which are conducted at a temperature of around 5° C. As illustrated in FIG. 3, the combination of glycerin 301, nitric acid 304, and solvent 302 in the first reaction vessel 320 at about 5° C. results in the production of mixed nitrate esters, predominantly 1,3-dinitroglycerine. The mixed nitrate esters are transferred with other byproducts of the reaction and unreacted reagents to the second reaction vessel 325 via product stream 306. The addition of caustic 308, such as sodium hydroxide, to the second reaction vessel 325 along with product stream 306 neutralizes most of the nitric acid 304 in product stream 306, producing sodium nitrate and water. Preferably, the caustic 308 may be introduced in solution form as a solution of between about 25 and 30% sodium hydroxide.

Sodium nitrate and water passed from the second reaction vessel 325 with product stream 309 may be separated from the dinitroglycerin and dichloromethane in product stream 309 using the first separation column 330. The separated brine 310 from the first separation column 330 includes water and sodium nitrate resulting from the reactions of the reagents in the first reaction vessel 320 and the second reaction vessel 325. The resulting product stream 311 from the first separation column 330 is fed to the third reaction vessel 335 and includes dinitroglycerin with some unreacted nitric acid, sodium nitrate, and dichloromethane. Additional caustic 312, preferably as a solution of between about 25 and 30% sodium hydroxide, is also added to the third reaction vessel 335 to convert the dinitroglycerin fed as product stream 311 to water, glycidyl nitrate, and sodium nitrate. Water, sodium hydroxide and some sodium nitrate resulting from the reaction within the third reaction vessel 335 may be removed as brine 314 from product stream 313 using the second separation column 340. Glycidyl nitrate and dichloromethane in product stream 315 may be separated from any remaining sodium nitrate using the third separation column 345 and the addition of sodium chloride in solution. The sodium chloride strips the sodium nitrate from the desired product and is purged from the process as brine 317. The resulting final product stream 318 includes glycidyl nitrate and dichloromethane ready to be used in a PGN production process.

The process of the present invention presents many advantages over other glycidyl nitrate production processes. One advantage of the invention process is the increased nitration yield over previous batch production processes. The nitration yield of the inventive process is at least about 80 percent and as high as about 90 percent-unexpectedly high compared to the 50 to 60 percent nitration rates experienced with batch reactions. It is believed that the skewed reaction kinetics of the continuous process account for the increase in nitration experienced with this process. In addition, surprisingly high selectivity of the reaction in the continuous mode was observed. The continuous mode produced, almost completely, a single isomer of 1,3-DNG, while the process in the batch mode produced a statistical distribution of isomers.

The production of glycidyl nitrate from glycerin, nitric acid, and caustic according to the process of the present invention also reduces hazardous waste. The addition of other glycidyl nitrate production processes. Without the presence of nitrate esters, the waste streams created in the present process are sewerable aqueous wastes. In other words, the brine streams may be processed in standard wastewater treatment facilities, thereby eliminating any need for additional, specialized waste treatment processes and equipment and reducing the overall operating costs of the process.

It was also observed that the glycidyl nitrate is not stable in the caustic and the brine, so the nitrate ester decomposes over time. Therefore, the caustic and the brine may be heated, such as to approximately 150° F., to remove the nitrate esters. Once the nitrate esters are removed, the solution may be neutralized with an inexpensive acid and processed in standard wastewater treatment facilities.

Another unique characteristic of the process of the present invention is that conventional continuous processing equipment may be used to produce glycidyl nitrate. Unlike other glycidyl nitrate processes, specialized reactors and equipment are not required to operate the inventive process. Instead, a glycidyl nitrate production plant may be fabricated from equipment readily available in commerce. In addition, the process of the present invention may be adapted to operate with a conventional production plant, such as with a Biazzi nitrator.

The continuous nature of the process and the use of common chemical production equipment allow the process to be scaled to achieve the desired production levels. The process may be scaled up or down by changing the amounts of reagents and the size of equipment used in the process. Thus, the process may be scaled up or down to meet the needs of a PGN production facility or the market.

Safety is also promoted using the process of the present invention. The resultant glycidyl nitrate is pure enough for polymerization without the need for purification or for dangerous distillation processes as used with other glycidyl nitrate processes. In addition, the use of the organic solvent dichloromethane within the process serves to dilute the energetic intermediate 1,3-dinitroglycerine as well as the monomer nitrate ester glyn, thereby reducing the opportunity for explosions during the production of glycidyl nitrate. The solvent dichloromethane is also a product used in the polymerization reaction of glycidyl nitrate to form PGN. Thus, the presence of the solvent with the glycidyl nitrate product is advantageous in that it may be fed directly to a PGN production process without further reaction or combination. In addition, dichloromethane removed during a PGN production process may be recycled for use in the process of the present invention, thereby reducing organic wastes and waste treatment requirements.

The overall costs of production using the process of the present invention may be lower than the costs of conventional glycidyl nitrate production processes. The chemical reagents used in the present process are relatively inexpensive, with a total reagent cost of less than ten dollars per pound of glycidyl nitrate produced in terms of present day pricing. In addition, the present process may be carried out at between 0° C. and 25° C. and, preferably, at about 5° C.; thus, temperature extremes are not incurred and additional costs for chilling equipment or to maintain low temperatures during the glycidyl nitrate production process are avoided. Furthermore, the cost of production equipment is minimized because existing, conventional equipment may be used rather than specialized or custom equipment. The continuous nature of the process also reduces the overall labor costs for the production process.

Figure 5:
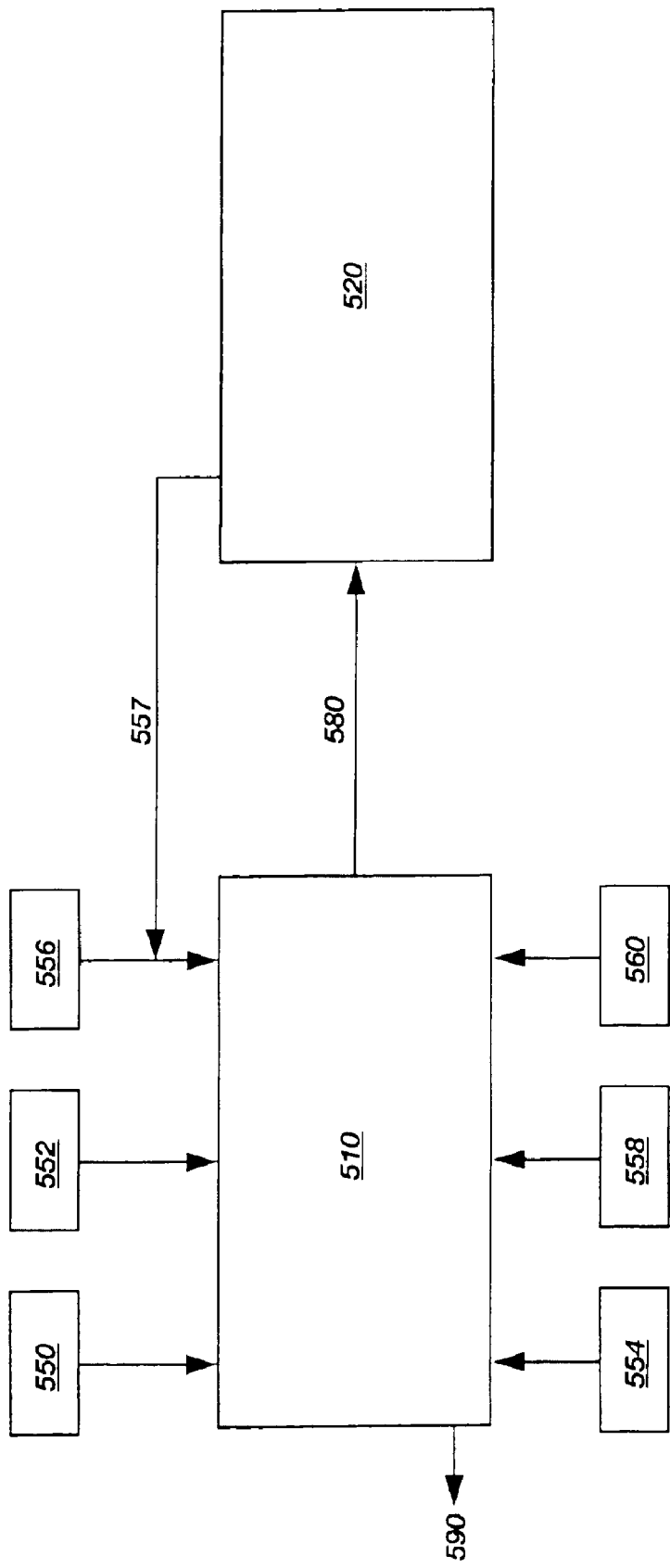
FIG. 5 illustrates a block diagram of the process of the present invention in a commercial PGN production process.

A simplified block diagram illustrating an exemplary combination of the process of the present invention with a PGN production process for the commercial production of propellants, explosives, gasifiers, or the like is illustrated in FIG. 5. Various chemicals and reagents are supplied to a process of the present invention 510 for the production of glycidyl nitrate. The chemicals and reagents supplied may include glycerin 550, nitric acid 552, caustic 554, solvent 556, air 558, and sodium chloride 560. The brine streams produced by the process of the present invention 510 may be combined as a single waste stream 590 that may be sent to a wastewater treatment facility. The product stream 580 from the process of the present invention 510 includes glycidyl nitrate. For safety reasons, the product stream 580 may also include a solvent 556, such as dichloromethane, that may also be used in the PGN process 520. The product stream 580 is passed from the process of the present invention 510 to the PGN process 520 for the production of desired products using the glycidyl nitrate produced by the process of the present invention 510. A solvent recycle stream 557 may be fed from the PGN process 520 to the solvent 556 input for the process of the present invention 510 in order to recycle and preserve solvent 556 used in both processes.

Figure 2:
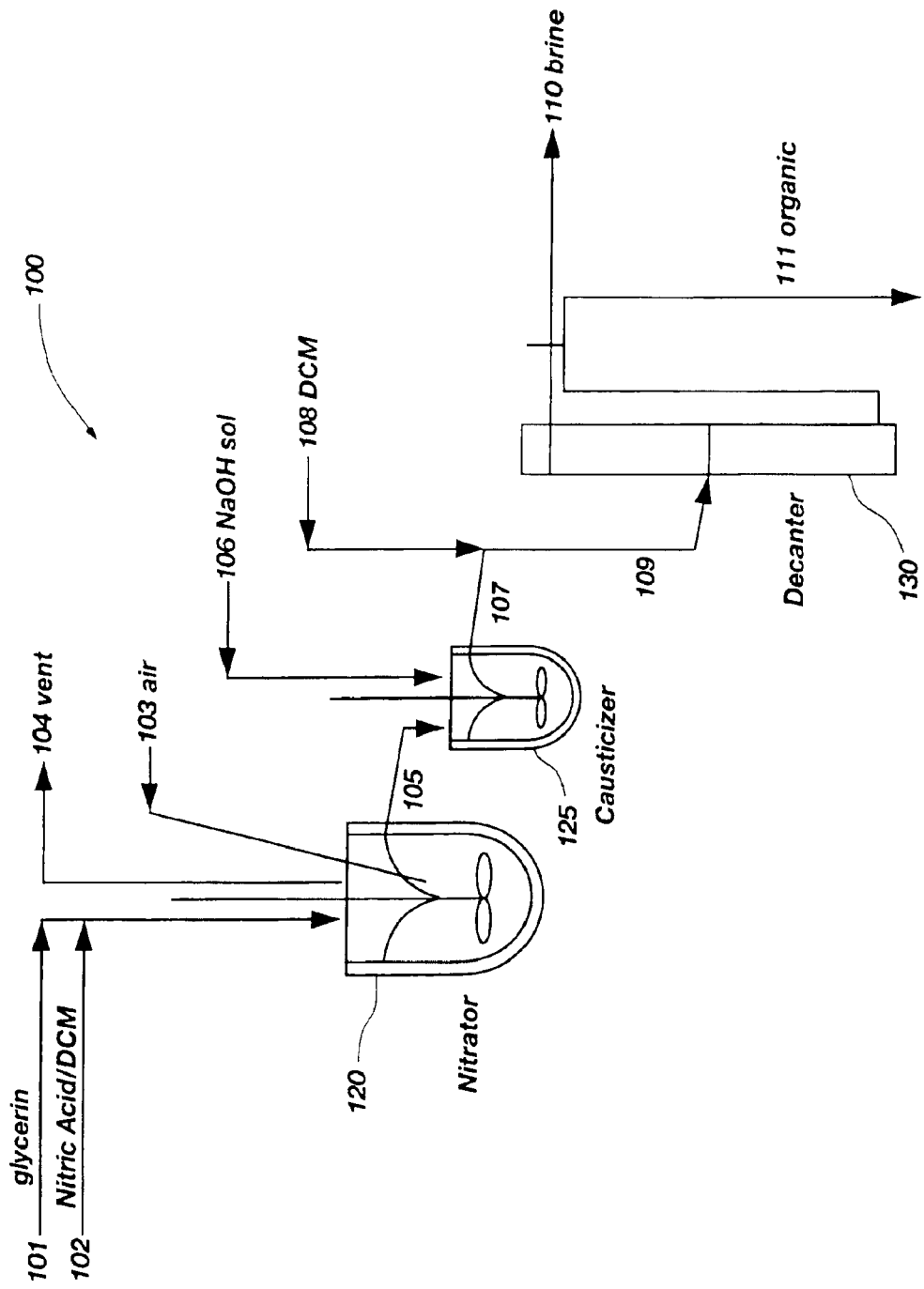
FIG. 2 illustrates a flow diagram of a modeled glycidyl nitrate production process shown in FIG. 1 having reagent and product flows as listed in Table I.
Figure 4:
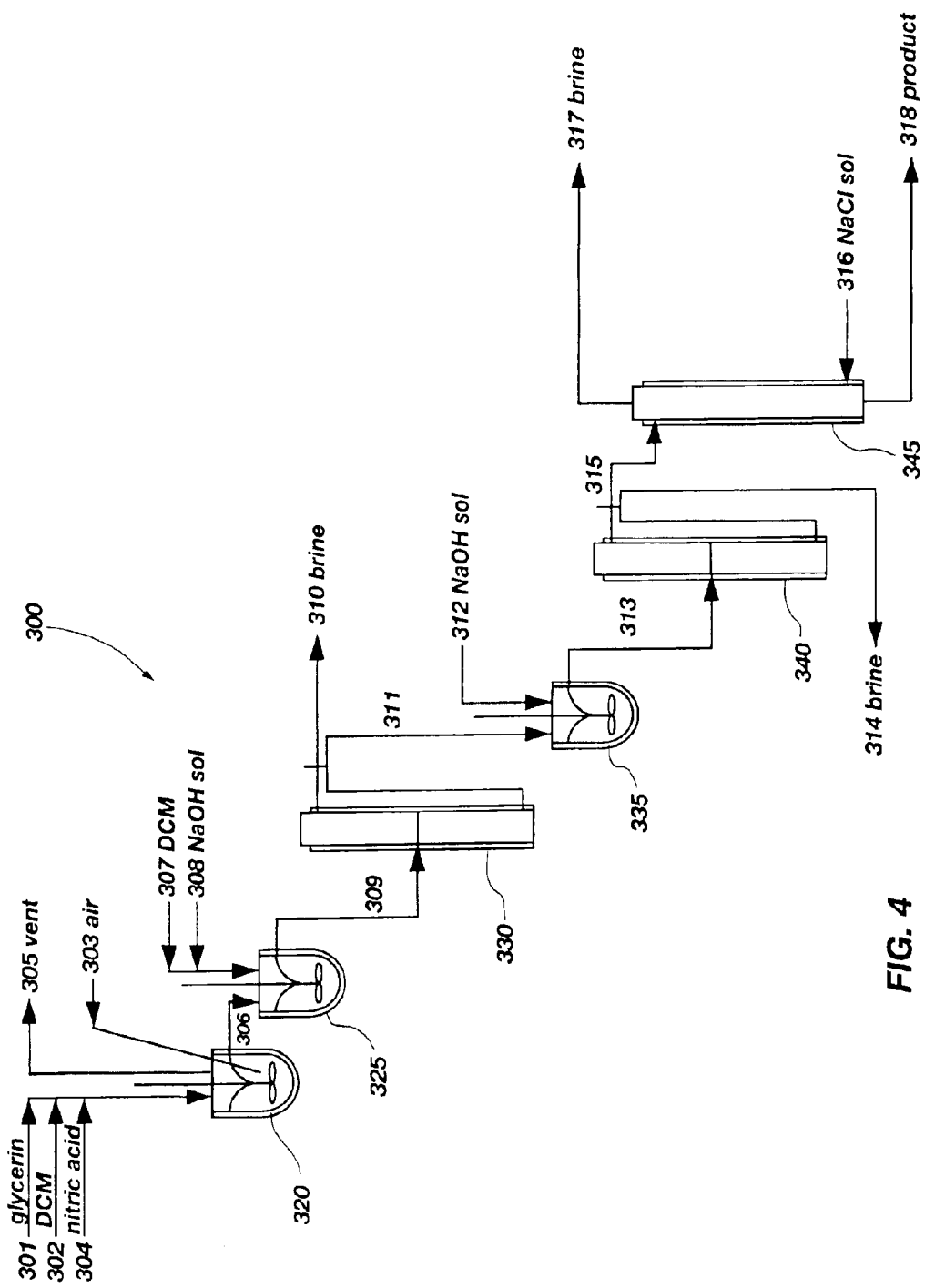
FIG. 4 illustrates a flow diagram of a modeled glycidyl nitrate production process shown in FIG. 3 having reagent and product flows as listed in Table II.

Models of the process of the present invention for the process systems illustrated in FIGS. 1 and 3 were created using ChemCad™ computer simulation software by Chemstations, Inc., (Houston, Tex.). Illustrations of the process equipment and relative reagent and product streams for the models are illustrated in FIGS. 2 and 4. Table I includes a listing of the flow rates (in grams per hour) of the components of the various reagents and product streams for the modeled process illustrated in FIG. 2 and Table II includes a listing of the flow rates (in grams per hour) of the components of the various reagents and product streams for the modeled process illustrated in FIG. 4. Tables I and II also illustrate the temperatures of the various reagent and product streams for the respective process system models.

TABLE I

| | \multicolumn{11}{c}{Stream Number} | | | | | | | | | | |
|---|---|---|---|---|---|---|---|---|---|---|---|
| | 101 | 102 | 103 | 104 | 105 | 106 | 107 | 108 | 109 | 110 | 111 |
| Stream Name | glycerin | Nitric acid/ dichloromethane | air | vent | PRODUCT | NaOH solution | PRODUCT | dichloro- methane | PRODUCT | brine | ORGANIC |
| Temperature °C. | 5 | 5 | 20 | 5 | 15 | 10 | | 10 | 15 | 10 | −19.7 |
| grams/Hour | 617 | 3014 | 427 | 588 | 3470 | 6204 | 976 | 1594 | 11268 | 8373 | 2896 |
| | | | | | Component Flow Rates (grams/hr) | | | | | | |
| Glycerol | 617 | 0 | 0 | 0 | 0 | 0 | 0 | 0 | 0 | 0 | 0 |
| Dichloromethane | 0 | 1073 | 0 | 153 | 920 | 0 | 920 | 1594 | 2514 | 50 | 2463 |
| Air | 0 | 0 | 610 | 610 | 0 | 0 | 0 | 0 | 0 | 0 | 0 |
| Nitric Acid | 0 | 1902 | 0 | 5.83 | 1052 | 0 | 0 | 0 | 0 | 0 | 0 |
| Dinitroglycerin | 0 | 0 | 0 | 0 | 1220 | 0 | 366 | 0 | 366 | 355 | 13 |
| Water | 0 | 39 | 0 | 1.86 | 279 | 4653 | 5317 | 0 | 5317 | 5314 | 3 |
| Sodium Hydroxide | 0 | 0 | 0 | 0 | 0 | 1551 | 696 | 0 | 696 | 696 | 0 |
| Glycidyl Nitrate | 0 | 0 | 0 | 0 | 0 | 0 | 558 | 0 | 558 | 143 | 415 |
| Sodium Nitrate | 0 | 0 | 0 | 0 | 0 | 0 | 1817 | 0 | 1817 | 1815 | 2 |

TABLE II

| | \multicolumn{9}{c}{Stream Number} | | | | | | | | |
|---|---|---|---|---|---|---|---|---|---|
| | 301 | 302 | 303 | 304 | 305 | 306 | 307 | 308 | 309 |
| Stream Name | glycerin | dichloromethane | air | nitric acid | vent | PRODUCT | dichloromethane | NaOH solution | PRODUCT |
| Temperature °C. | 5 | 5 | 20 | 5 | 5 | 5 | 10 | 10 | 5 |
| grams/Hour | 617 | 814 | 427 | 1941 | 889 | 2910 | 259 | 2158 | 5327 |
| | | | | Component Flow Rates (grams/hr) | | | | | |
| Glycerin | 617 | 0 | 0 | 0 | 0 | 0 | 0 | 0 | 0 |
| Dichloromethane | 0 | 814 | 0 | 0 | 421 | 393 | 259 | 0 | 652 |
| Air | 0 | 0 | 427 | 0 | 427 | 0 | 0 | 0 | 0 |
| Nitric Acid | 0 | 0 | 0 | 1902 | 37 | 1020 | 0 | 0 | 4 |
| Dinitroglycerin | 0 | 0 | 0 | 0 | 0 | 1220 | 0 | 0 | 1220 |
| Water | 0 | 0 | 0 | 39 | 3 | 277 | 0 | 1513 | 2081 |
| Sodium Hydroxide | 0 | 0 | 0 | 0 | 0 | 0 | 0 | 645 | 0 |
| Glycidyl Nitrate | 0 | 0 | 0 | 0 | 0 | 0 | 0 | 0 | 0 |
| Sodium Nitrate | 0 | 0 | 0 | 0 | 0 | 0 | 0 | 0 | 1371 |
| Sodium Chloride | 0 | 0 | 0 | 0 | 0 | 0 | 0 | 0 | 0 |

| | \multicolumn{9}{c}{Stream Number} | | | | | | | | |
|---|---|---|---|---|---|---|---|---|---|
| | 310 | 311 | 312 | 313 | 314 | 315 | 316 | 317 | 318 |
| Stream Name | brine | PRODUCT | NaOH solution | PRODUCT | brine | PRODUCT | NaCl solution | PRODUCT | FINAL PRODUCT |
| Temperature °C. | 5 | 5 | 15 | 10 | 10 | 10 | 15 | −19.69 | 15 |
| grams/Hour | 3299 | 2028 | 976 | 3004 | 1379 | 1625 | 1830 | 2005 | 1450 |
| | | | | Component Flow Rates (grams/hr) | | | | | |
| Glycerin | 0 | 0 | 0 | 0 | 0 | 0 | 0 | 0 | 0 |
| Dichloromethane | 0 | 652 | 0 | 652 | 0 | 652 | 0 | 0 | 652 |
| Air | 0 | 0 | 0 | 0 | 0 | 0 | 0 | 0 | 0 |
| Nitric Acid | 0 | 4 | 0 | 0 | 0 | 0 | 0 | 0 | 0 |
| Dinitroglycerin | 0 | 1220 | 0 | 0 | 0 | 0 | 0 | 0 | 0 |

TABLE II-continued

| | | | | | | | | | |
|---|---|---|---|---|---|---|---|---|---|
| Water | 2081 | 0 | 683 | 805 | 805 | 0 | 1647 | 1647 | 0 |
| Sodium Hydroxide | 0 | 0 | 293 | 22 | 22 | 0 | 0 | 0 | 0 |
| Glycidyl Nitrate | 0 | 0 | 0 | 798 | 0 | 798 | 0 | 0 | 798 |
| Sodium Nitrate | 1218 | 152 | 0 | 727 | 552 | 175 | 0 | 175 | 0 |
| Sodium Chloride | 0 | 0 | 0 | 0 | 0 | 0 | 183 | 183 | 0 |

Having thus described certain preferred embodiments of the present invention, it is to be understood that the present invention is not limited by particular details set forth in the above description, as many apparent variations thereof are possible without departing from the spirit or scope thereof as hereinafter claimed.

What is claimed is:

1. A process for producing glycidyl nitrate, comprising:
  feeding glycerin and nitric acid to a first reaction vessel;
  reacting the glycerin and the nitric acid in the first reaction vessel to produce a nitrate ester that consists essentially of 1,3-dinitroglycerin and nitric acid;
  withdrawing at least a portion of the nitrate ester that consists essentially of 1,3-dinitroglycerin and nitric acid from the first reaction vessel;
  feeding sodium hydroxide and the withdrawn portion of the nitrate ester that consists essentially of 1,3-dinitroglycerin and nitric acid to a second reaction vessel;
  reacting the sodium hydroxide and the withdrawn portion of nitric acid in the second reaction vessel to neutralize the nitric acid;
  withdrawing a product from the second reaction vessel, the product comprising the nitrate ester that consists essentially of 1, 3-dinitroglycerin, water, and sodium nitrate;
  separating the nitrate ester that consists essentially of 1,3-dinitroglycerin from the water;
  feeding sodium hydroxide and the separated nitrate ester that consists essentially of 1,3-dinitroglycerin to a third reaction vessel;
  reacting the separated nitrate ester that consists essentially of 1,3-dinitroglycerin and the sodium hydroxide within the third reaction vessel to produce glycidyl nitrate and byproducts;
  withdrawing the glycidyl nitrate and the byproducts from the third reaction vessel; and
  separating the glycidyl nitrate from the byproducts.

2. The process of claim 1, further comprising feeding dichloromethane to the first reaction vessel.

3. The process of claim 1, further comprising feeding dichloromethane to the second reaction vessel.

4. The process of claim 1, further comprising performing the process in a continuous manner.

5. The process of claim 1, wherein reacting the glycerin and the nitric acid in the first reaction vessel, reacting the sodium hydroxide and the withdrawn portion of nitric acid in the second reaction vessel, and reacting the separated nitrate ester that consists essentially of 1,3-dinitroglycerin and the sodium hydroxide within the third reaction vessel comprises performing the reactions at a temperature ranging from about 0° C. to about 25° C.

6. The process of claim 1, wherein reacting the glycerin and nitric acid in the first reaction vessel comprises performing the reaction at about 5° C.

7. The process of claim 1, wherein feeding the glycerin and the nitric acid to the first reaction vessel comprises feeding the glycerin and the nitric acid to the first reaction vessel at about 5° C.

8. The process of claim 1, wherein feeding sodium hydroxide and the withdrawn portion of the nitrate ester that consists essentially of 1,3-dinitroglycerin and nitric acid to the second reaction vessel comprises feeding sodium hydroxide and the withdrawn portion of the nitrate ester that consists essentially of 1,3-dinitroglycerin and nitric acid to the second reaction vessel at about 5° C.

9. The process of claim 1, wherein feeding the sodium hydroxide and the separated nitrate ester that consists essentially of 1,3-dinitroglycerin to the third reaction vessel comprises feeding the sodium hydroxide and the separated nitrate ester that consists essentially of 1,3-dinitroglycerin to the third reaction vessel at about 5° C.

10. A process for producing glycidyl nitrate, comprising:
  reacting glycerin and nitric acid to produce a first product comprising nitric acid, a nitrate ester that consists essentially of 1,3-dinitroglycerin, and water;
  reacting the first product and sodium hydroxide to neutralize the nitric acid and produce a second product comprising nitric acid, the nitrate ester that consists essentially of 1,3-dinitroglycerin, water, and sodium nitrate;
  removing water and sodium nitrate from the second product to produce a third product;
  reacting the third product and sodium hydroxide to produce a fourth product comprising water, sodium hydroxide, glycidyl nitrate and sodium nitrate; and
  separating the glycidyl nitrate from the fourth product.

11. The process of claim 10, wherein reacting the glycerin and the nitric acid to produce the first product comprises:
  feeding the glycerin to a first reaction vessel;
  feeding the nitric acid to the first reaction vessel; and
  mixing the glycerin and the nitric acid within the first reaction vessel.

12. The process of claim 11, further comprising feeding a solvent to the first reaction vessel with the glycerin and the nitric acid.

13. The process of claim 12, further comprising selecting the solvent to be dichloromethane.

14. The process of claim 11, wherein mixing the glycerin and the nitric acid within the first reaction vessel comprises mixing the glycerin and the nitric acid with a stirring mechanism.

15. The process of claim 11, further comprising mixing the glycerin and the nitric acid at about 5° C.

16. The process of claim 10, wherein reacting the first product and the sodium hydroxide to produce the second product comprises:
  feeding the first product to a second reaction vessel;
  feeding sodium hydroxide to the second reaction vessel; and
  mixing the first product and the sodium hydroxide in the second reaction vessel.

17. The process of claim 16, further comprising feeding a solvent to the second reaction vessel.

18. The process of claim 17, wherein feeding the solvent to the second reaction vessel comprises feeding dichloromethane to the second reaction vessel.

19. The process of claim 16, wherein mixing the first product and the sodium hydroxide in the second reaction vessel comprises mixing the first product and the sodium hydroxide with a stirring mechanism.

20. The process of claim 16, wherein mixing the first product and the sodium hydroxide in the second reaction vessel comprises mixing the first product and the sodium hydroxide at about 5° C.

21. The process of claim 10, wherein removing the water and the sodium nitrate from the second product to produce the third product comprises:

feeding the second product to a separation column; and removing the water and the sodium nitrate from the second product in the separation column to form a brine stream and the third product.

22. The process of claim 21, wherein the brine stream comprises the removed water and sodium nitrate from the second product.

23. The process of claim 21, wherein removing the water and the sodium nitrate from the second product in the separation column to form the brine stream and the third product comprises removing the water and the sodium nitrate from the second product in the separation column to form the brine stream and nitric acid, the nitrate ester that consists essentially of 1,3-dinitroglycerin, and sodium nitrate.

24. The process of claim 10, wherein separating the glycidyl nitrate from the fourth product comprises removing water, sodium hydroxide, and sodium nitrate from the fourth product.

25. The process of claim 24, wherein removing water, sodium hydroxide, and sodium nitrate from the fourth product comprises:

feeding the fourth product to a separation column; and removing the water, sodium hydroxide and sodium nitrate from the fourth product in the separation column to produce a brine stream and a fifth product comprising glycidyl nitrate and sodium nitrate.

26. The process of claim 25, wherein the brine stream comprises the removed water, sodium hydroxide, and sodium nitrate.

27. The process of claim 25, further comprising:

feeding the fifth product to a second separation column; and feeding sodium chloride to the second separation column to remove the sodium nitrate from the fifth product to produce a brine stream and glycidyl nitrate.

28. A method for producing glycidyl nitrate in a continuous process, comprising:

continuously feeding glycerin, dichloromethane, and nitric acid to a first reaction vessel;

mixing the glycerin, dichloromethane, and nitric acid within the first reaction vessel to promote a reaction between the glycerin and the nitric acid to produce a first product;

withdrawing the first product from the first reaction vessel;

feeding the first product and sodium hydroxide to a second reaction vessel;

mixing the first product and the sodium hydroxide within the second reaction vessel to promote a reaction between the first product and the sodium hydroxide to produce a second product;

withdrawing the second product from the second reaction vessel;

feeding the second product to a first separation column;

separating a third product from the second product in the first separation column, wherein the third product comprises a nitrate ester that consists essentially of 1,3-dinitroglycerin feeding the third product and sodium hydroxide to a third reaction vessel;

mixing the third product and the sodium hydroxide within the third reaction vessel to promote a reaction between the nitrate ester that consists essentially of 1,3-dinitroglycerin in the third product and the sodium hydroxide to produce a fourth product comprising glycidyl nitrate;

withdrawing the fourth product from the third reaction vessel;

feeding the fourth product to a second separation column;

separating glycidyl nitrate, dichloromethane, and sodium nitrate from the fourth product in the second separation column;

feeding the separated glycidyl nitrate, dichloromethane, and sodium nitrate to a third separation column;

feeding sodium chloride to the third separation column;

separating the lycidyl nitrate and the dichloromethane from the sodium nitrate and sodium chloride in the third separation column; and withdrawing the lycidyl nitrate and the dichloromethane from the third separation column as a final product.

29. The method of claim 28, further comprising feeding dichloromethane to the second reaction vessel.

30. The method of claim 28, wherein mixing the glycerin, dichloromethane, and nitric acid within the first reaction vessel to promote the reaction between the glycerin and the nitric acid to produce the first product comprises mixing the glycerin, dichloromethane, and nitric acid within the first reaction vessel to promote a reaction between the glycerin and the nitric acid to produce dichloromethane, nitric acid, the nitrate ester that consists essentially of 1,3-dinitroglycerin, and water.

31. The method of claim 28, wherein mixing the first product and the sodium hydroxide within the second reaction vessel to promote the reaction between the first product and the sodium hydroxide to produce the second product comprises mixing the first product and the sodium hydroxide within the second reaction vessel to promote a reaction between the first product and the sodium hydroxide to produce dichloromethane, the nitrate ester that consists essentially of 1,3-dinitroglycerin, water, and sodium nitrate.

32. The method of claim 31, wherein the second product further comprises nitric acid.

33. The method of claim 28, wherein the method is carried out between about 0° C. and about 25° C.

34. A system for producing glycidyl nitrate, comprising:

a first reaction vessel for reacting glycerin and nitric acid to produce a nitrate ester that consists essentially of 1,3-dinitroglycerin, the first reaction vessel comprising a feed input for receiving glycerin and nitric acid and an output for withdrawing a first product from the first reaction vessel;

a second reaction vessel for reacting sodium hydroxide with the first product, the second reaction vessel comprising a second feed input for receiving sodium hydroxide and the first product from the output of the first reaction vessel and a second output for withdrawing a second product from the second reaction vessel;

a separation column for receiving the second product and separating the nitrate ester that consists essentially of 1,3-dinitroglycerin from the second product, the separation column comprising a column input for receiving the second product, a column output for withdrawing the separated ester that consists essentially of 1,3-dinitroglycerin, and a column waste stream for withdrawing products separated from the nitrate ester that consists essentially of 1,3-dinitroglycerin from the separation column;

a third reaction vessel for reacting sodium hydroxide and the separated nitrate ester that consists essentially of 1,3-dinitroglycerin, the third reaction vessel comprising a third feed input for receiving the sodium hydroxide and the separated nitrate ester that consists essentially of 1,3-dinitroglycerin and a third output for withdrawing a third product; and a separation unit for receiving the third product and separating glycidyl nitrate from the third product, the separation unit comprising a separation unit input for receiving the third product, a separation unit output for withdrawing the separated glycidyl nitrate from the separation unit, and a separation unit waste stream for withdrawing products separated from the glycidyl nitrate from the separation unit.

35. The system of claim 34, wherein the separation unit comprises:

a first separation column, comprising a first input for receiving the third product, a first output for withdrawing a separated product from the first separation column, and a first waste stream; and a second separation column, comprising a second input for receiving the separated product from the first output, a third input for receiving sodium chloride solution, a second output for withdrawing the separated glycidyl nitrate, and a second waste stream.

36. The system of claim 34, further comprising a stirring mechanism for mixing the contents of at least one of the first reaction vessel, the second reaction vessel, and the third reaction vessel.

37. A process for producing glycidyl nitrate, comprising:

reacting glycerin and nitric acid to produce a first product comprising nitrate ester that consists essentially of 1,3-dinitroglycerin; and reacting the first product with a caustic to produce glycidyl nitrate and byproducts.

38. The process of claim 37, wherein reacting the first product with the caustic comprises reacting the first product with sodium hydroxide.

39. The process of claim 37, wherein reacting the first product with the caustic comprises reacting the first product with a solution of sodium hydroxide.

40. The process of claim 37, further comprising separating the glycidyl nitrate from the byproducts.

41. The process of claim 37, further comprising:

reacting the glycerin and the nitric acid in the presence of a solvent; and reacting the first product with a caustic in the presence of the solvent.

42. The process of claim 41, wherein reacting the first product with the caustic in the presence of the solvent comprises reacting the first product with the caustic in the presence of dichloromethane.

43. The process of claim 37, further comprising neutralizing the nitric acid in the first product with a caustic.

44. The process of claim 37, further comprising:

separating the glycidyl nitrate from the byproducts; and polymerizing the glycidyl nitrate to produce poly(glycidyl nitrate).

45. A process for producing poly(glycidyl nitrate), comprising:

reacting glycerin and nitric acid to produce a first product comprising nitrate ester that consists essentially of 1,3-dinitroglycerin;

reacting the nitrate ester that consists essentially of 1,3-dinitroglycerin with a caustic to produce glycidyl nitrate and byproducts;

separating the glycidyl nitrate from the byproducts; and polymerizing the glycidyl nitrate to produce poly(glycidyl nitrate).

46. The process of claim 45, wherein reacting the glycerin and the nitric acid comprises reacting the glycerin and nitric acid in the presence of a solvent.

47. The process of claim 46, wherein reacting the glycerin and the nitric acid in the presence of the solvent comprises reacting the glycerin and the nitric acid in the presence of dichloromethane.

48. The process of claim 45, wherein reacting the nitrate ester that consists essentially of 1,3-dinitroglycerin with the caustic comprises reacting the nitrate ester that consists essentially of 1,3-dinitroglycerin with the caustic in the presence of a solvent.

49. The process of claim 48, wherein reacting the nitrate ester that consists essentially of 1,3-dinitroglycerin with the caustic in the presence of the solvent comprises reacting the nitrate ester that consists essentially of 1,3-dinitroglycerin with the caustic in the presence of dichloromethane.

50. The process of claim 45, further comprising neutralizing nitric acid in the first product with a sodium hydroxide solution.

51. The process of claim 45, wherein reacting the nitrate ester that consists essentially of 1,3-dinitroglycerin with the caustic comprises reacting the nitrate ester that consists essentially of 1,3-dinitroglycerin in said first product with sodium hydroxide.

52. The process of claim 45, wherein reacting the nitrate ester that consists essentially of 1,3-dinitroglycerin with the caustic comprises reacting said the nitrate ester that consists essentially of 1,3-dinitroglycerin in said first product with a solution of sodium hydroxide.

53. A process for producing poly(glycidyl nitrate), comprising:

reacting glycerin and nitric acid in the presence of a solvent to produce a first product comprising a nitrate ester that consists essentially of 1,3-dinitroglycerin;

reacting the nitrate ester that consists essentially of 1,3-dinitroglycerin with caustic in the presence of the solvent to produce glycidyl nitrate and byproducts;

separating the byproducts from the glycidyl nitrate and the solvent; and polymerizing the glycidyl nitrate in the presence of the solvent to produce poly(glycidy nitrate).

54. The process of claim 53, wherein reacting the glycerin and the nitric acid in the presence of the solvent comprises reacting the glycerin and the nitric acid in the presence of dichloromethane.

55. The process of claim 53, wherein reacting the nitrate ester that consists essentially of 1,3-dinitroglycerin with the caustic comprises reacting the nitrate ester that consists essentially of 1,3-dinitroglycerin with sodium hydroxide.

56. The process of claim 53, wherein reacting the nitrate ester that consists essentially of 1,3-dinitroglycerin with the caustic comprises reacting said the nitrate ester that consists essentially of 1,3-dinitroglycerin with a solution of sodium hydroxide.

57. The process of claim 53, wherein reacting the glycerin and the nitric acid in the presence of the solvent to produce the first product comprising the nitrate ester that consists essentially of 1,3-dinitroglycerin and reacting the nitrate ester that consists essentially of 1,3-dinitroglycerin with the caustic in the presence of the solvent to produce glycidyl nitrate and byproducts comprise performing the reactions at a temperature from about 0° C. to about 25° C.

58. A process for producing glycidyl nitrate, comprising:
feeding glycerin and nitric acid to a first reaction vessel;
reacting the glycerin and the nitric acid in the first reaction vessel to produce a nitrate ester that consists essentially of 1,3-dinitroglycerin and nitric acid;
withdrawing at least a portion of the nitrate ester that consists essentially of 1,3-dinitroglycerin and at least a portion of the nitric acid from the first reaction vessel;
feeding sodium hydroxide and the withdrawn portions of the nitrate ester that consists essentially of 1,3-dinitroglycerin and nitric acid to a second reaction vessel;
reacting the sodium hydroxide and the withdrawn portions of the nitrate ester that consists essentially of 1,3-dinitroglycerin and nitric acid in the second reaction vessel;
withdrawing a product comprising the nitrate ester that consists essentially of 1,3-dinitroglycerin, water, sodium nitrate, and glycidyl nitrate from the second reaction vessel; and
separating the glycidyl nitrate from the product.

59. The process of claim 58, further comprising feeding dichloromethane to the first reaction vessel.

60. The process of claim 59, wherein separating the glycidyl nitrate from the product comprises separating glycidyl nitrate and dichloromethane from the product.

61. The process of claim 58, further comprising combining dichloromethane with the product prior to separating the glycidyl nitrate from the product.

62. The process of claim 58, further comprising performing the process in a continuous manner.

63. The process of claim 58, wherein reacting the glycerin and the nitric acid in the first reaction vessel and reacting the sodium hydroxide and the withdrawn portions of the nitrate ester that consists essentially of 1,3-dinitroglycerin and nitric acid in the second reaction vessel comprise performing the reactions at a temperature from about 0° C. to about 25° C.

64. The process of claim 58, wherein reacting the glycerin and the nitric acid in the first reaction vessel and reacting the sodium hydroxide and the withdrawn portions of the nitrate ester that consists essentially of 1,3-dinitroglycerin and nitric acid in the second reaction vessel comprise performing the reactions at about 5° C.

65. A process for producing glycidyl nitrate, comprising:
reacting glycerin and nitric acid to produce a first product comprising nitric acid and a nitrate ester that consists essentially of 1,3-dinitroglycerin;
reacting the first product and sodium hydroxide to produce a second product comprising glycidyl nitrate; and
separating the glycidyl nitrate from the second product.

66. The process of claim 65, wherein reacting the glycerin and the nitric acid to produce the first product comprises:
feeding the glycerin to a first reaction vessel;
feeding the nitric acid to the first reaction vessel; and
reacting the glycerin and the nitric acid within the first reaction vessel.

67. The process of claim 66, further comprising feeding a solvent to the first reaction vessel.

68. The process of claim 67, wherein the solvent to the first reaction vessel comprises feeding dichloromethane to the first reaction vessel.

69. The process of claim 66, wherein reacting the glycerin and the nitric acid within the first reaction vessel comprises reacting the glycerin and the nitric acid at a temperature between about 0° C. and about 25° C.

70. The process of claim 65, wherein reacting the first product and the sodium hydroxide to produce the second product comprises:
feeding the first product to a second reaction vessel;
feeding sodium hydroxide to the second reaction vessel; and
reacting the first product and the sodium hydroxide in the second reaction vessel.

71. The process of claim 70, wherein feeding the sodium hydroxide to the second reaction vessel comprises feeding a sodium hydroxide solution to the second reaction vessel.

72. The process of claim 65, wherein separating the glycidyl nitrate from the second product comprises feeding the second product to a separation column to remove the glycidyl nitrate.

73. The process of claim 72, further comprising feeding dichloromethane to the separation column with the second product.

74. The process of claim 73, further comprising removing the glycidyl nitrate and dichloromethane using the separation column.

75. A method for producing glycidyl nitrate in a continuous process, comprising:
continuously feeding glycerin, dichloromethane and nitric acid to a first reaction vessel;
reacting the glycerin and the nitric acid in the first reaction vessel to form a first product comprising a nitrate ester that consists essentially of 1,3-dinitroglycerin;
withdrawing the first product from the first reaction vessel;
feeding the first product and sodium hydroxide to a second reaction vessel;
reacting the first product and the sodium hydroxide in the second reaction vessel to form a second product comprising glycidyl nitrate;
withdrawing the second product from the second reaction vessel;
feeding the second product to a separation column; and
separating the glycidyl nitrate from the second product in the separation column.

76. The method of claim 75, further comprising feeding dichloromethane to the first reaction vessel.

77. The method of claim 75, wherein feeding the second product to a separation column comprises:
combining the second product with dichloromethane; and
feeding the combined second product and dichloromethane to the separation column.

78. The method of claim 75, wherein reacting the glycerin and the nitric acid in the first reaction vessel and reacting the first product and the sodium hydroxide in the second reaction vessel comprise performing the reactions at a temperature between about 0° C. and about 25° C.

79. A system for producing glycidyl nitrate, comprising:

a first reaction vessel for reacting glycerin and nitric acid to produce a nitrate ester that consists essentially of 1,3-dinitroglycerin, the first reaction vessel comprising a feed input for receiving glycerin and nitric acid and an output for withdrawing a first product from the first reaction vessel;

a second reaction vessel for reacting sodium hydroxide with the first product to produce a second product, comprising glycidyl nitrate, the second reaction vessel comprising a second feed input for receiving sodium hydroxide and the first product from the output of the first reaction vessel and a second output for withdrawing the second product from the second reaction vessel; and a separation apparatus for receiving the second product and separating the nitrate ester that consists essentially of 1,3-dinitroglycerin from the second product, the separation apparatus comprising an input for receiving the second product, an output for withdrawing the separate nitrate ester that consists essentially of 1.3-dinitroglycerin, and a waste stream for withdrawing products separated from the nitrate ester that consists essentially of 1,3-dinitroglycerin from the separation apparatus.

80. The system of claim 79, wherein the separation apparatus is one of a separation column, a decanter, a centrifuge, a weir tank, a static separator, and a bucket.

81. The system of claim 79, further comprising a stirring mechanism for mixing contents of at least one of the first reaction vessel and said the second reaction vessel.

82. The method of claim 1, wherein reacting the glycerin and the nitric acid in the first reaction vessel to produce the nitrate ester that consists essentially of 1,3-dinitroglycerin and nitric acid comprises achieving a nitration yield of at least approximately 50 percent.

83. The method of claim 2, wherein reacting the glycerin and the nitric acid in the first reaction vessel to produce the nitrate ester that consists essentially of 1,3-dinitroglycerin and nitric acid comprises achieving a nitration yield ranging from at least approximately 80 percent to approximately 90 percent.

* * * * *

UNITED STATES PATENT AND TRADEMARK OFFICE
CERTIFICATE OF CORRECTION

| | | |
|---|---|---|
| PATENT NO. | : 6,870,061 B2 | Page 1 of 2 |
| APPLICATION NO. | : 10/340167 | |
| DATED | : March 22, 2005 | |
| INVENTOR(S) | : Thomas K. Highsmith and Harold E. Johnston | |

It is certified that error appears in the above-identified patent and that said Letters Patent is hereby corrected as shown below:

On the title page:
In ITEM (57) ABSTRACT
  LINE 7  change "vessel, a second" to
        --system includes a vessel, a second--

In the specification:

| | | |
|---|---|---|
| COLUMN 1, | LINE 11, | change "provide" to --provided-- |
| COLUMN 1, | LINE 45, | change "to on" to --to its rate of reaction-- |
| COLUMN 1, | LINE 47, | change "chloride, ed" to --chloride, may also be added-- |
| COLUMN 1, | LINE 65, | change "chances" to --changes-- |
| COLUMN 2, | LINES 41-43, | change "nitrate are not economically feasible for the large-scale commercial production of glycidyl nitrate." to --nitrate.-- |
| COLUMN 2, | LINE 61, | change "nitrates" to --nitrate-- |
| COLUMN 2, | LINE 63, | change "nitric is" to --nitric acid is-- |
| COLUMN 3, | LINE 63, | change "lycidyl" to --glycidyl-- |
| COLUMN 5, | LINE 57, | change "100281 Production" to --Production-- |
| COLUMN 6, | LINE 59, | change "0° C. and" to --0° C. to approximately 25° C., and-- |
| COLUMN 9, | LINES 59, 60 | after "The addition of" and before "other" insert --caustic 308 within the system 300 helps to eliminate harmful nitrate esters that are often found in-- |

In the claims:

| | | |
|---|---|---|
| CLAIM 1, | COLUMN 13, LINE 34, | change "1, 3-dinitroglycerin," to --1,3-dinitroglycerin,-- |

Signed and Sealed this
Twenty-third Day of February, 2016

Michelle K. Lee
*Director of the United States Patent and Trademark Office*

| CLAIM 28, | COLUMN 16, | LINE 7,  | change "dinitroglycerin" to --dinitroglycerin;-- and start a new line beginning with "feeding the third product" |
| CLAIM 28, | COLUMN 16, | LINE 25, | change "lycidyl nitrate" to --glycidyl nitrate-- |
| CLAIM 28, | COLUMN 16, | LINE 28, | change "lycidyl nitrate" to --glycidyl nitrate-- |
| CLAIM 51, | COLUMN 18, | LINE 40, | change "1,3-dinitroglycerin in said first product with" to --1,3-dinitroglycerin with-- |
| CLAIM 52, | COLUMN 18, | LINE 45, | change "1,3-dinitroglycerin in said first product with" to --1,3-dinitroglycerin with-- |
| CLAIM 53, | COLUMN 18, | LINE 59, | change "poly(glycidy" to --poly(glycidyl-- |
| CLAIM 56, | COLUMN 19, | LINE 3,  | change "said the nitrate" to --the nitrate-- |
| CLAIM 68, | COLUMN 20, | LINE 7,  | change "wherein the" to --wherein feeding the-- |